US012265372B2

(12) United States Patent
Chevalier et al.

(10) Patent No.: US 12,265,372 B2
(45) Date of Patent: Apr. 1, 2025

(54) ANALYSIS OF BODY-SIDE PERFORMANCE DIFFERENCES USING ACTIVITY-BASED DATA COLLECTION DEVICES

(71) Applicant: TheConnectedGrip, Inc., San Jose, CA (US)

(72) Inventors: Vincent Le Chevalier, San Jose, CA (US); William Vablais, Indian Wells, CA (US)

(73) Assignee: TheConnectedGrip, Inc., San Jose, CA (US)

( * ) Notice: Subject to any disclaimer, the term of this patent is extended or adjusted under 35 U.S.C. 154(b) by 247 days.

(21) Appl. No.: 17/694,631

(22) Filed: Mar. 14, 2022

(65) Prior Publication Data

US 2022/0206462 A1 Jun. 30, 2022

Related U.S. Application Data

(63) Continuation of application No. 16/589,015, filed on Sep. 30, 2019, now abandoned, which is a
(Continued)

(51) Int. Cl.
*G05B 19/4099* (2006.01)
*A61B 5/107* (2006.01)
(Continued)

(52) U.S. Cl.
CPC ........ *G05B 19/4099* (2013.01); *A61B 5/1079* (2013.01); *A61B 5/1125* (2013.01);
(Continued)

(58) Field of Classification Search
CPC ...... G05B 19/4099; G05B 2219/35134; G05B 2219/49004; G05B 2219/49007;
(Continued)

(56) References Cited

U.S. PATENT DOCUMENTS 5,299,457 A * 4/1994 Pang .................... G01L 1/24
482/47
5,681,993 A * 10/1997 Heitman .............. A61B 5/225
473/202
(Continued)

FOREIGN PATENT DOCUMENTS

CN 204671798 U 9/2015

OTHER PUBLICATIONS

Su et al. "Ontological Knowledge Engine and Health Screening Data Enabled Ubiquitous Personalized Physical Fitness (UFIT)," Sensors 2014, 14, pp. 4560-4584 (2014); doi:10.3390/s140304560.
(Continued)

*Primary Examiner* — Yuhui R Pan
(74) *Attorney, Agent, or Firm* — Huse IP Law; Charles C. Huse

(57) ABSTRACT

Sensor data are obtained for an activity performed by a user. The sensor data include data from one or more sensors in one or more grips gripped by the user's left hand and the user's right hand during the activity. The sensor data are analyzed to identify a difference in performance of the activity between the left side of the user's body and the right side of the user's body. Feedback is provided to the user to compensate for the difference.

10 Claims, 10 Drawing Sheets

Related U.S. Application Data continuation of application No. 15/483,653, filed on Apr. 10, 2017, now Pat. No. 10,429,822.

(60) Provisional application No. 62/321,688, filed on Apr. 12, 2016.

(51) Int. Cl.

| | | |
|---|---|---|
| *A61B 5/11* | (2006.01) | |
| *A63B 24/00* | (2006.01) | |
| *A61B 5/00* | (2006.01) | |
| *A61B 5/0205* | (2006.01) | |
| *A61B 5/024* | (2006.01) | |
| *A61B 5/0533* | (2021.01) | |
| *A61B 5/145* | (2006.01) | |
| *A61B 5/22* | (2006.01) | |

(52) U.S. Cl.
CPC ........... *A61B 5/02055* (2013.01); *A61B 5/024* (2013.01); *A61B 5/0533* (2013.01); *A61B 5/1118* (2013.01); *A61B 5/14542* (2013.01); *A61B 5/225* (2013.01); *A61B 5/6825* (2013.01); *A61B 5/7264* (2013.01); *A61B 2560/0242* (2013.01); *A61B 2560/0425* (2013.01); *A61B 2562/0219* (2013.01); *A63B 24/0062* (2013.01); *G05B 2219/35134* (2013.01); *G05B 2219/49004* (2013.01); *G05B 2219/49007* (2013.01)

(58) Field of Classification Search
CPC . A61B 5/1079; A61B 5/1125; A61B 5/02055; A61B 5/024; A61B 5/0533; A61B 5/1118; A61B 5/14542; A61B 5/225; A61B 5/318; A61B 5/6825; A61B 5/7264; A61B 2560/0242; A61B 2560/0425; A61B 2562/0219; A63B 24/0062

See application file for complete search history.

(56) References Cited

U.S. PATENT DOCUMENTS

| | | | |
|---|---|---|---|
| 6,918,862 B1* | 7/2005 | Comeau | A63B 23/16 |
| | | | 482/44 |
| 2003/0074766 A1 | 4/2003 | Tillim | |
| 2004/0044273 A1* | 3/2004 | Keith | A61B 5/224 |
| | | | 600/300 |
| 2007/0021687 A1 | 1/2007 | Keith et al. | |
| 2009/0144921 A1 | 6/2009 | Newsome | |
| 2010/0063944 A1* | 3/2010 | Grogan | G16H 20/30 |
| | | | 705/500 |
| 2012/0277891 A1 | 11/2012 | Aragones et al. | |
| 2013/0079693 A1 | 3/2013 | Ranky et al. | |
| 2013/0090212 A1 | 4/2013 | Wang | |
| 2013/0143718 A1 | 6/2013 | Pani et al. | |
| 2014/0366650 A1 | 12/2014 | Thillainadarajah et al. | |
| 2015/0032236 A1 | 1/2015 | Yu et al. | |
| 2015/0245789 A1* | 9/2015 | Dromerick | A61B 5/1124 |
| | | | 600/558 |
| 2016/0120276 A1 | 5/2016 | Lair | |
| 2016/0220863 A1* | 8/2016 | Braier | A63B 23/16 |
| 2016/0253890 A1* | 9/2016 | Rabinowitz | G08B 21/0461 |
| | | | 340/539.13 |
| 2017/0278419 A1 | 9/2017 | Wells et al. | |
| 2017/0368413 A1 | 12/2017 | Shavit | |
| 2018/0067545 A1 | 3/2018 | Provancher et al. | |

OTHER PUBLICATIONS

U.S. Appl. No. 17/207,604, Non-Final Office Action, Sep. 29, 2022.

\* cited by examiner

Grip Strength

| Rating | Males (lbs) | Males (kg) | Females (lbs) | Females (kg) |
|---|---|---|---|---|
| Excellent | >141 | >64 | >84 | >38 |
| Very Good | 123-141 | 56-64 | 75-84 | 34-38 |
| Above Average | 114-122 | 52-55 | 66-74 | 30-33 |
| Average | 105-113 | 48-51 | 57-65 | 26-29 |
| Below average | 96-104 | 44-47 | 49-56 | 23-25 |
| Poor | 88-95 | 40-43 | 44-48 | 20-22 |
| Very poor | <88 | <40 | <44 | <20 |

Figure 10

ANALYSIS OF BODY-SIDE PERFORMANCE DIFFERENCES USING ACTIVITY-BASED DATA COLLECTION DEVICES

RELATED APPLICATIONS

This application is a continuation of U.S. patent application Ser. No. 16/589,015, filed Sep. 30, 2019, which is a continuation of U.S. patent application Ser. No. 15/483,653, filed Apr. 10, 2017, issued as U.S. Pat. No. 10,429,822, which claims the benefit of U.S. Provisional Application No. 62/321,688, filed Apr. 12, 2016. All of these applications are incorporated herein by reference in their entirety.

TECHNICAL FIELD

This invention generally relates to data collection by sensors. More specifically, the present invention relates to modeling grip interfaces used to provide information about users to various connected devices.

BACKGROUND

The current generation of fitness, health and sports activity trackers are defined by a typically passive always-on capture and aggregation of users' activities data over the course of day/week and month timeframe. This type of general purpose data capture, along with its simple dashboard representation, while presenting some benefit to the users, is inherently constrained by its basic lack of real-time contextual information from the activities actually performed by the users, thus limiting the value of that data to a one-way experience with limited user feedback, coaching or interactions from other users sharing similar interests.

While the various products that we interact with are getting increasingly customized, by contrast, the grip, as the main and only contextual physical connection between a product and its user, has remained remarkably unchanged. This provides an opportunity to rethink and disrupt the accepted shape and function of this valuable human interface form-factor for both the consumer and professional markets.

SUMMARY OF THE INVENTION

The "System and method for building activity-based data collection devices" describes a new range of devices and contextual applications based on the users' interactions with a simple grip-metaphor design for many B2B and B2C offerings.

By embedding an array of real-time sensors for health, environmental and other datasets using embedded microcontroller network technology and focusing on the grip, as the contextual interface between the physical and virtual [data] worlds, value-added applications and services to existing "grip-based devices" becomes generic but also integrated into many market opportunities, such as sports, fitness equipment, health monitoring, activity tracking, coaching, physical therapy, mobility aide and virtual entertainment, among others.

BRIEF DESCRIPTION OF THE DRAWINGS

Referring now to the attached drawings which form a part of the original disclosure:

FIG. 10 shows an average rating of grip strength for men and women.

DETAILED DESCRIPTION

The activity-based data collection devices is architected around 4 main components and related systems, as listed: Connected grip embedded system; The user of a connected grip; Paired mobile applications; and Contextual analytic platform and application.

Figure 1:
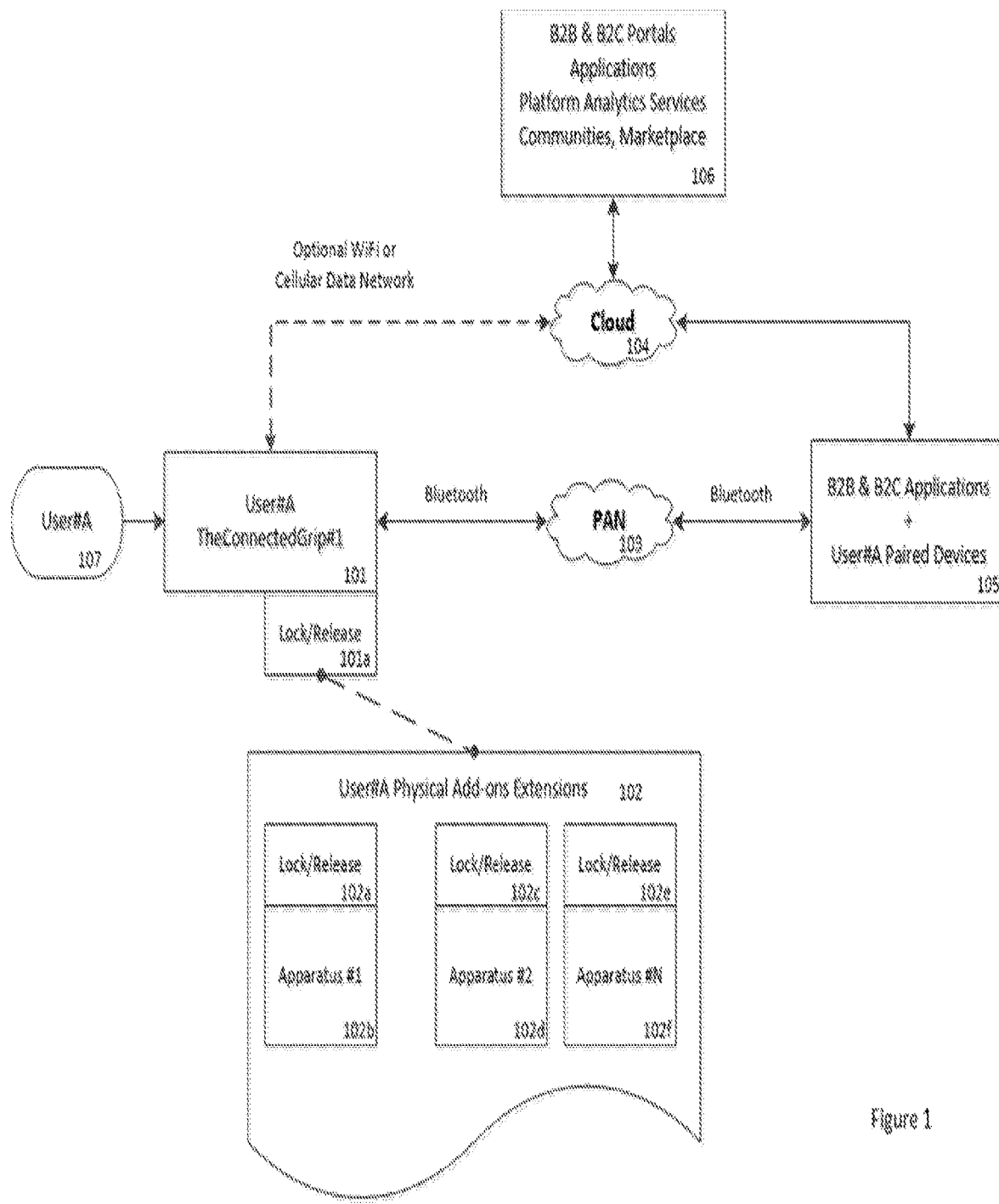
FIG. 1 illustrates the 3 main components of the activity-based data collection devices and applications.

FIG. 1 illustrates the 4 components of the activity-based data collection system.

As illustrated in FIG. 1, the user 107 is engaging in one more physical activities with a connected grip embedded system 101 by attaching one or more physical extensions 102 via a quick connect lock and release mechanism 101a.

The connected grip embedded system 101 is paired to a connected device applications 105, such as a smartphone or tablet, via a wireless integrated personal area network 103, i.e. PAN, such as Bluetooth. Other wireless networks, such as WiFi or cellular data networks may also be integrated with a connected grip 101 for providing cloud connectivity 104 to the platform applications 106. The connected grip 101 real-time activity-based data is captured, encrypted and securely uploaded over available wireless networks to the paired mobile application 105 and platform 106.

The paired connected device application 105 is visualizing the captured encrypted data from the connected grip 101 while uploading the processed data to the contextual analytic platform 106 for additional processing and services.

Activity-based services are typically based on a combination of data visualization, personalized recommendations, coaching, social interchange and online marketplace resulting for analytic and artificial intelligence algorithms applied to the aggregated user activity data.

Single User Mode

By definition, a connected grip 101 is specifically designed to be held and operated by the hand of a user 107.

Depending on the type of activities, a user 107 can interact with 2 connected grips 101 simultaneously, one for its left hand and the other for its right hand. Other configurations may include interacting with 3, 4 or more connected grips 101.

Figure 2:
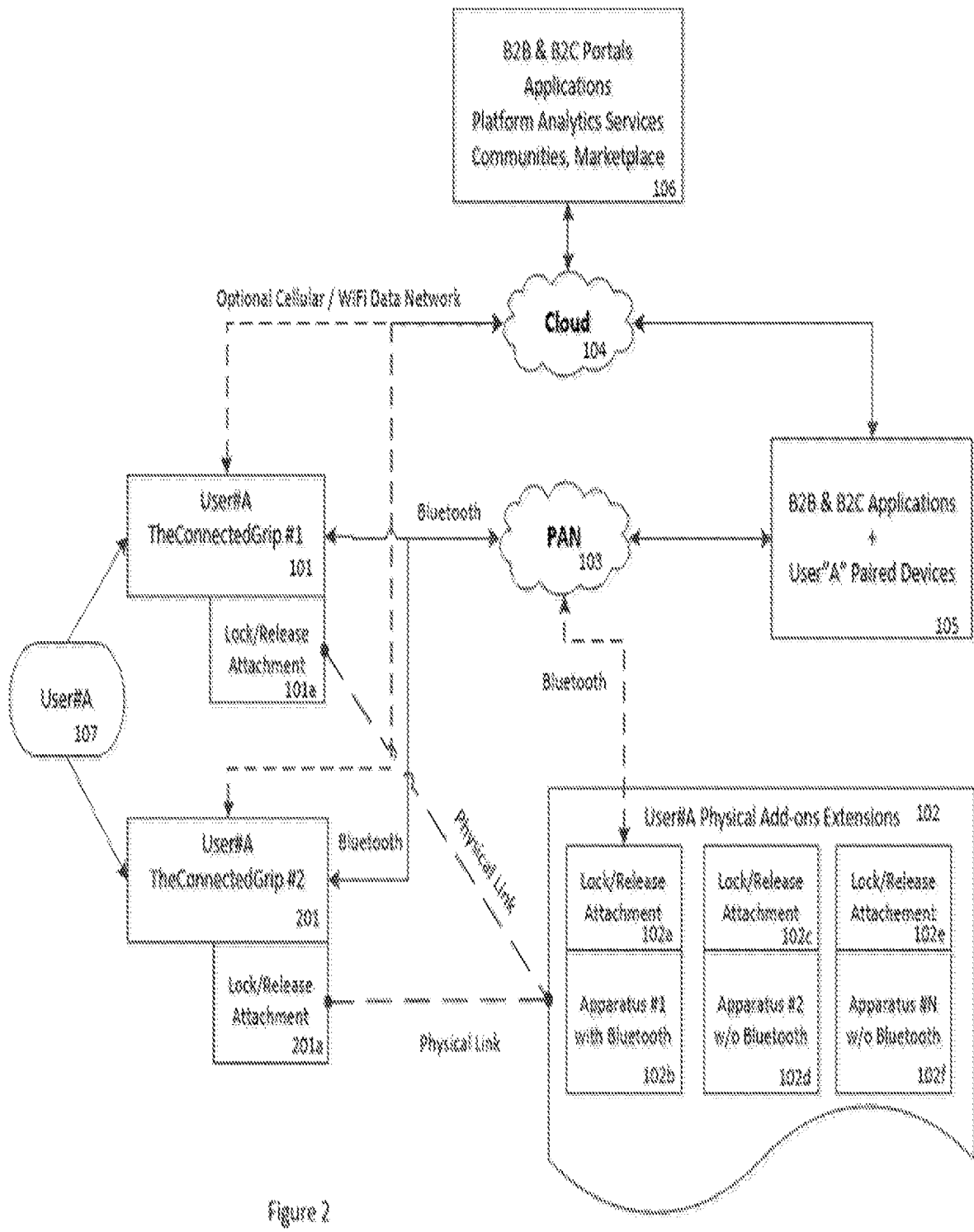
FIG. 2 illustrates a set of 2 connected grips paired to the user's connected device and applications.

FIG. 2 illustrates user #A 107 engaging with a set of 2 connected grips 101 and 201, which are both paired to a connected device 105 in a dual-mode activity-based contextual analytic platform. In dual-mode activities, the connected grips 101 and 201 are connected over the same PAN 103 and streaming real-time activity-based data captured from activi-} ties performed from both the left and right hands of user #A 107 when engaging with connected grips 101 and 201.

In dual-mode activities, the connected grips 101 and 201 can be physically attached to specific apparatus 102 via their quick-connect lock and release mechanism in synchronous or asynchronous mode.

For example, an elastic band apparatus 102c and its lock and release mechanism 102d may be physically attached a connected grip 101 and 201 using their respective lock and release attachments 101a and 201a.

As another example, a weighted jump rope apparatus 102b and its lock and release mechanism 102a may include a wireless connection such as Bluetooth to be able to capture the moment of inertia of the rotating weighted rope.

When interacting with a set of 2 connected grips 101 and 201, the contextual analytic platform 106 and applications 105 are analyzing the real-time activities performed jointly by the left and right side of user #A body 107, effectively enabling a comparison between each side given similar activities. This provides for actionable feedback to user #A 107 by being able to focus on a set of personalized activities programmed and delivered by the platform 106 that overtime compensate for the measured differences between both sides of its body, such as relative strength and balance for examples.

Multiple Users Mode

When multiple users interact with their respective set of connected grips, the contextual analytic platform enables selected synchronization services that process the incoming user activity-based data when engaging in the same type of activities. This enables the platform services to correlate a particular user activity with another user of similar activity, profile, or with a group of users, providing access to likeminded social communities, personalized feedback, individual coaching, group coaching or competitive events.

Figure 3:
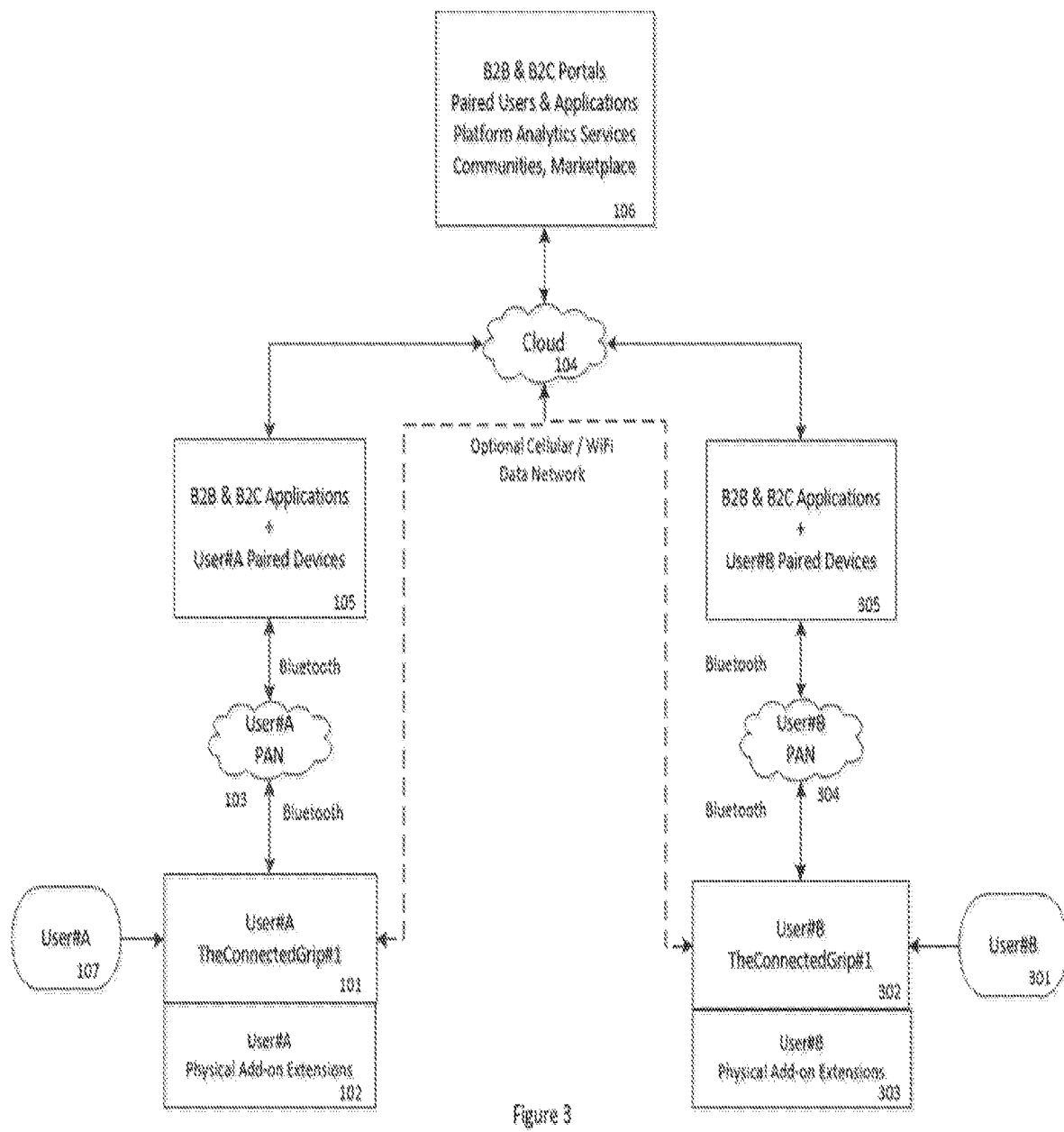
FIG. 3 illustrates 2 distinct users, each interacting with one connected grip in activity-based contextual applications.

FIG. 3 illustrates 2 distinct users, user #A 107 and user #b 301, with user #a interacting with connected grip 101 and extension 102 while user #B is interacting with connected grip 302 with extension 303, both connected to the contextual analytic platform 106.

In multiple users mode, the contextual activity platform performs the aggregation and synchronization of the incoming data streams from each connected grips as captured by the paired mobile applications, enabling 2 or more users to interact with other users based on similar activities.

For example, a group of users engaging in jump rope activities, may perform the same type of activities, either synchronously or not, as managed by the platform applications and services 106.

Connected Grip Embedded System Processes

The connected grip embedded systems 101 are modeled and architected from the following processes: Hand grip modeling and classification; Mechanical hardware design; Embedded integrated circuits, sensors and printed circuit board; Embedded software stack and application; and Supporting cloud service.

Hand Grip Modeling and Classification

A connected grip is by definition held in the hand of a user while it is actively engaged with a particular activity, such as fitness, sports, physical therapy or other grip-based product activities. This particular type of human interface requires a form factor and ergonomic design as comfortable and practical to its user as possible.

In addition, because various external sensors may be located on the external surface of a connected grip, it is important to place these particular external sensors into the most favorable locations that correspond to the fingers, palm and hand area of the user when interacting with the external sensors of a connected grip.

Because grip-based products come in different types and shapes, the grip of an existing product typically ranges between a generic cylinder, such as a tube for example, to a more complex ergonomic design, such as a ski pole for example, which may follows the contours and details of someone's hand. In both cases, the grip of these products is typically based on a cylinder of a particular diameter which is encapsulated into a protective substrate layer, such as plastic for example.

To support this requirement, a modeling process comparable to other hand-based products, such as gloves for example, is implemented, resulting in the classifying of connected grips into predetermined sizes, effectively matching an average grip size to the users' hand classification system.

Based on the type of connected grip products and activities, there are 2 distinct processes as listed: Semi customized (extra small, small, medium, large and extra-large for examples); and Fully customized (personalized to the hand of an individual).

The semi customized process is built from the capture, processing and mathematical analysis of pictures of hands, built from a database of users' hands, to calculate the dimensions of someone's hand and its related classifications. The calculated 2D hand surface area properties are then projected onto a 3 dimensional surface area to determine the grip surface area that corresponds best to a specific grip-based product.

The fully customized process is similar in term of analysis without adhering to the hand classification model, instead projecting someone hand's dimensions into a fully customized grip-based ergonomic design fully compatible with a particular hand's physical requirements.

Calculating the Hand Surface Area (HSA)

Figure 4:
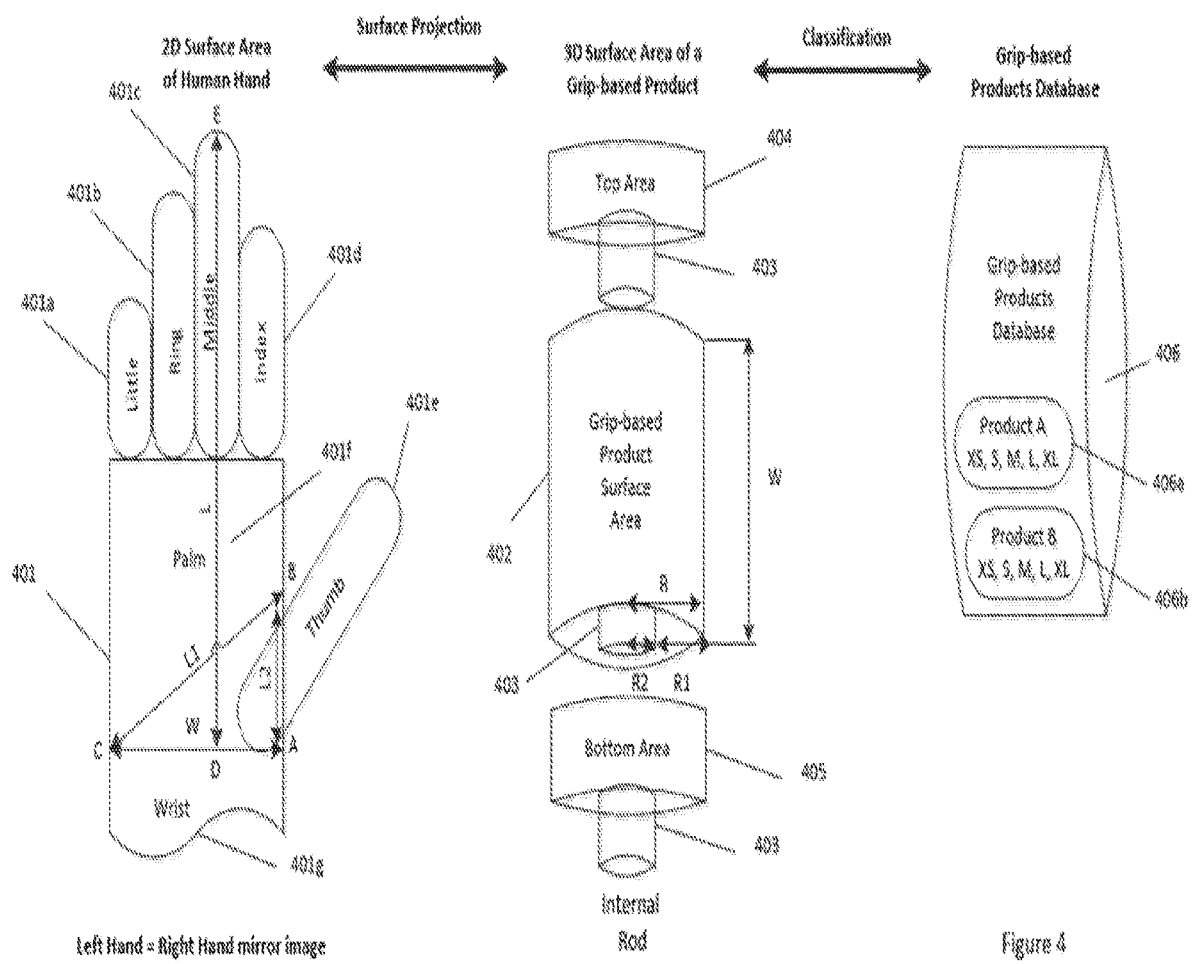
FIG. 4 illustrates the 2D surface area projection and classification of someone's hand onto a 3 dimensional model.

FIG. 4 illustrates the modeling and classification of someone's hands.

As illustrated FIG. 4, the human hands come in various sizes and shapes. In order to determine and classify someone's hand, it is necessary to calculate its approximate surface area and compare it with other hands for classification.

A typical hand 401 comprises a little finger 401a, a ring finger 401b, a middle finger 401c, an index finger 401d, a thumb 401e, a palm 401f and a wrist 401d.

Starting from a scan, or picture, of someone's hand resting on a flat support 401, the surface area of that hand (S) is typically expressed as a product of its length (L) by its width (W), with W referenced by the wrist location and L defined as the distance between the wrist 401g and the tip E of the middle finger 401c. The result is a close approximation, typically within a few percent "N", (+/−2-3%) of the actual surface area of that hand, as expressed by the following equation:

$$\text{Total Hand Surface area (HSA)} = (W \times L) + N\%$$

The computed hand surface area (HSA) value S is then compared with other computed hand surface areas to classify that hand against an existing library of various hand sizes, typically segmented into extra-small, small, medium, large and extra-large. Other sizes can be added based on the level of customization to apply to the model.

This method does not apply to the hands of individuals who suffer from possible injuries or illness, resulting in different shapes and sizes outside of what one would expect from a fully normal and operating hand. As a result, assumptions are made as to what a standard set of hands look like, reducing the degree of customization for the semi-customized algorithm.

Calculating the Hand Grippable Surface Area (GSA)

The hand surface area that is "compatible" with grip-based product activities is defined as the "grip surface area", i.e. GSA, and is a subset of the total "hand surface area", i.e. HSA.

The GSA is expressed as the difference between HSA and a triangle surface area defined by the thumb intersection with the wrist, point A, thumb intersection with the palm, point B, and Point C located across the hand on the opposite side of point A. The distance L2 between point A and B, the distance W between Point A and C and distance L1 between points B and C determines the surface area of a triangle which has little value for external sensors location, as expressed by the following equation:

Total Grip Surface Area (GSA)=HSA−(($W/2$)×$L2$)

The "grip hand surface" area (GSA) value is then compared with other GSA values to classify that particular hand against an existing library of various hand sizes, effectively providing another validation point for the hand classification model.

Grip Modeling Dimensions

Generally, grips are represented as 3 segments, defined as top 404, middle 402 and bottom 405 areas. The middle segment 402 is typically the location of the external sensors which are interacting directly with the hand touching them. The top 404 and bottom 405 segment areas are typically containers for electronics, battery and other internal sensors.

The 2D "grip surface area" GSA is projected onto the middle segment 402 of the grip expressed initially as a 3 dimensional cylinder with no indentations. By projecting the GSA onto a cylinder, the value of GSA remains constant and equivalent to the value of the "lateral surface area", i.e. LSA, of the grip-like cylinder, as expressed by the following equation:

Grip Surface Area (GSA)=Grip Middle Lateral Surface Area (LSA)

GSA=LSA=$2\pi(R) \times H$; with $H$ (height)>=$W$ and $R$ (cylinder radius)

When applied to a grip-cylinder with no internal rod 403, the "lateral surface area" LSA is determined by the equation:

HSA−(($W/2$)×$L2$)=$2\pi(R) \times W$, from which variable radius $R$ is computed When applied to a grip-cylinder with an internal rod 403 of a constant radius R2, the "lateral surface area" is determined by the equation:

HSA−(($W/2$)×$L2$)=$2\pi(R1+R2) \times W$, from which variable radius $R2$ is computed The optimum grip dimensions are derived directly from the above equation.

Other 3 Dimensional Grip Modeling

The same above process for calculating the "lateral surface area" of a 3 dimensional object is also applied for grips of different geometric shapes, such as a cone, truncated cone, cube, pipe, pyramid, rectangular box, a sphere, a torus, a triangle prism, a tube or others, effectively building a grip-based products database 406.

As indicated previously, the grip "lateral surface area" is naturally optimized when the "grip surface area" GSA is equal or nearly equal to the grip middle "lateral surface area" LSA. It is however possible to design grip-based products where the total grip middle "lateral surface area" is significantly larger than the "grip surface area". This is the case for example for grip-based products which the hand cannot close completely around, for instance with a 3 dimensional object significantly larger than the hand, such as a large spear, bocce ball, bowling or a heavy rowing oar, for examples.

In the above examples, the "grip surface area" may represent only a fraction of the total grip "middle lateral surface" area. However, the location of the various external sensors in relation to the "grip surface area" and related hand classification remains effectively constant. The external sensors have to make contact with their designated hand surface area locations regardless of the 3 dimensional object total middle "lateral surface area".

As another example, the grip "middle lateral surface" area of a 3 dimensional object can also be represented as a sleeve from a grip-based product perspective. With the addition of the required external sensors, a sleeve can be modeled for existing 3 dimensional grip-based products, effectively providing an add-on to these existing products and database 406.

Connected Grip Modeling Dimensions with Indentation Levels

The indentations applied to a connected grip 101 bring an ergonomic level of customization for that grip-based product. As the original 3 dimensional "lateral surface area" expands to reflect the level of indentations that result from modeling various fingers lengths and shapes into the "lateral surface area", the increase in surface area is globally expressed by a factor Z that corresponds to the level of indentation being applied.

The "lateral surface area" of a cylinder grip lateral surface area with indentations is then determined by the equation= (($2\pi(R1+R2) \times W$)+Z %

In above equation, Z is expressed as a % associated to a particular indentation level, defined as low, medium and high, with value ranging from 5% to 15% based on indentation level.

As indicated in previous section, the same above process for calculating the "lateral surface area" with indentations of a 3 dimensional object can be applied for grips of different geometric shapes, such as a cone, truncated cone, cube, pipe, pyramid, rectangular box, a sphere, a torus, a triangle prism, a tube, sleeves or others.

Connected Grip Models Database

The grip models database 406 comprises all the various 3 dimensional grips which have been computed for a particular grip-based product, based on the hand classification.

For instance, a particular grip-product 406a is going to have multiple grip models, one corresponding to each classification, with dimensions computed to match the classification.

For example, the extra-small, small, medium, large and extra-large hands are matched with corresponding extra-small, small, medium, large and extra-large grip models.

Hand Classifications and Grip External Surface Sensors Modeling

The external surface sensors that are embedded into the connected grips 101 are characterized by their size requirements, geometric shapes and relative location within the surface area of the hand that interact with them.

Their size requirements and geometric shapes are typically a constant parameter defined by the manufacturer of the type of sensors being used. For instance, a particular external sensor may require a certain rectangle geometric shape expressed as X by Y millimeters. This requirement implies that the location of that external sensor onto the grip "lateral surface area" is to be at least equivalent to the required shape and size for that external sensor. Similarly, other external surface sensors may require a different shape of different size based on their respective types and locations.

These requirements do not change given the variations resulting from hands classification. For instance, the external surface requirements are the same regardless of the extra-small, small, medium, large and extra-large grip models. However, the locations of these external surface sensors need to be adjusted based on the amount of "lateral surface area" available, as computed previously.

The external surface sensors which are embedded into a connected grip 101 include various types of sensors, including, but not limited to: force/pressure, pulse include any combination of oximetry, heart rate, ECG, body temperature, galvanic skin response sensors and fingerprint for example.

Figure 5:
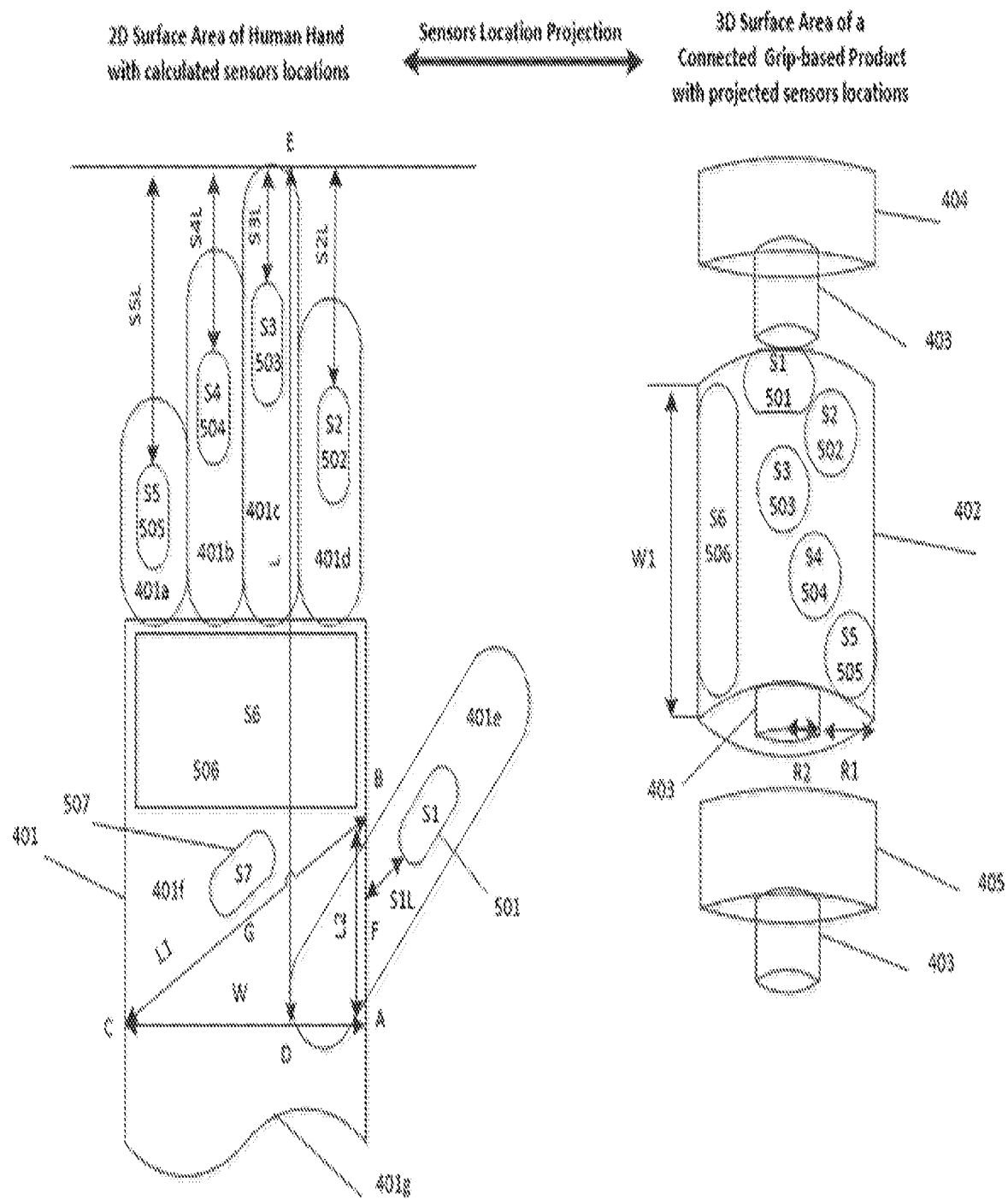
FIG. 5 illustrates the positioning of external surface sensors between a 2D surface area and projected 3 dimensional model.

FIG. 5 illustrates the relative positioning of various external surface sensors based on the hand classifications.

As indicated in FIG. 5, the various areas for external surface sensors in a connected grip 101 are identified by multiple distinct locations, typically including sensor S1 501 for the thumb 401e, sensor S2 502 for the index 401d, sensor S3 503 for the middle finger 401c, sensor S4 504 for the ring finger 401b, sensor S5 505 for the little finger 401a, sensor S6 506 for the palm area 501f and sensor S7 507 below the palm area.

For each finger located sensors, specific sensor-compatible location are calculated in reference to the tip of the middle finger 401c, identified by the top of the hand 401 referenced by point E on FIG. 5.

For instance, the sensor surface area S2 502 is located at a distance of S2L from the top of the hand 401 as identified by the tip of the middle finger located by point E. Similarly, the sensors surface area S3, S4 and S5 are located at distances S3L, S4L and S5L from top of the hand 401 as referenced by Point E in relation to their respective fingers.

From the anatomy of the hand 401, the S2, S3, S4 and S5 sensor respective locations 502, 503, 504 and 505 typically overlap between the medium and distal phalanges of their respective fingers. It is also possible to adjust that surface area to include all phalanges of a particular finger, or any fraction of a phalange, based on the individual sensor surface area requirements.

The sensor surface area S1 501 is located at the tip of the thumb 401e and is referenced at a distance of S1L from point B, identified as the intersection between the thumb 401e and the palm 401f. For the anatomy of the hand 401, the S1 sensor location 501 typically overlaps between the proximal and distal phalanges of the thumb 401e. It is also possible to adjust that surface area to include all phalanges of a thumb, or any fraction of a phalange, based on the individual sensor surface area requirements.

The sensor surface area S7 507 is centered above point G located in the middle of a straight line defined between point B and C. S7 is typically placed below the sensor area S6 and next to the edge of the "grip surface area".

The sensor surface area S6 506 is typically overlapping the palm area 401f of the hand 401, or a fraction of it, and is computed as the area below the start of the fingers and above point B line. The particularity of the sensors area S6 506 is to be large enough to handle several types of sensors, including for example heart rate, pulse oximetry, temperature and pressure resistance.

Hand to Grip Modeling Classification Flowchart

The hand to grip process of modeling classification is implemented based on the 2 distinct Hand Modeling and Grip Modeling processes.

Figure 6:
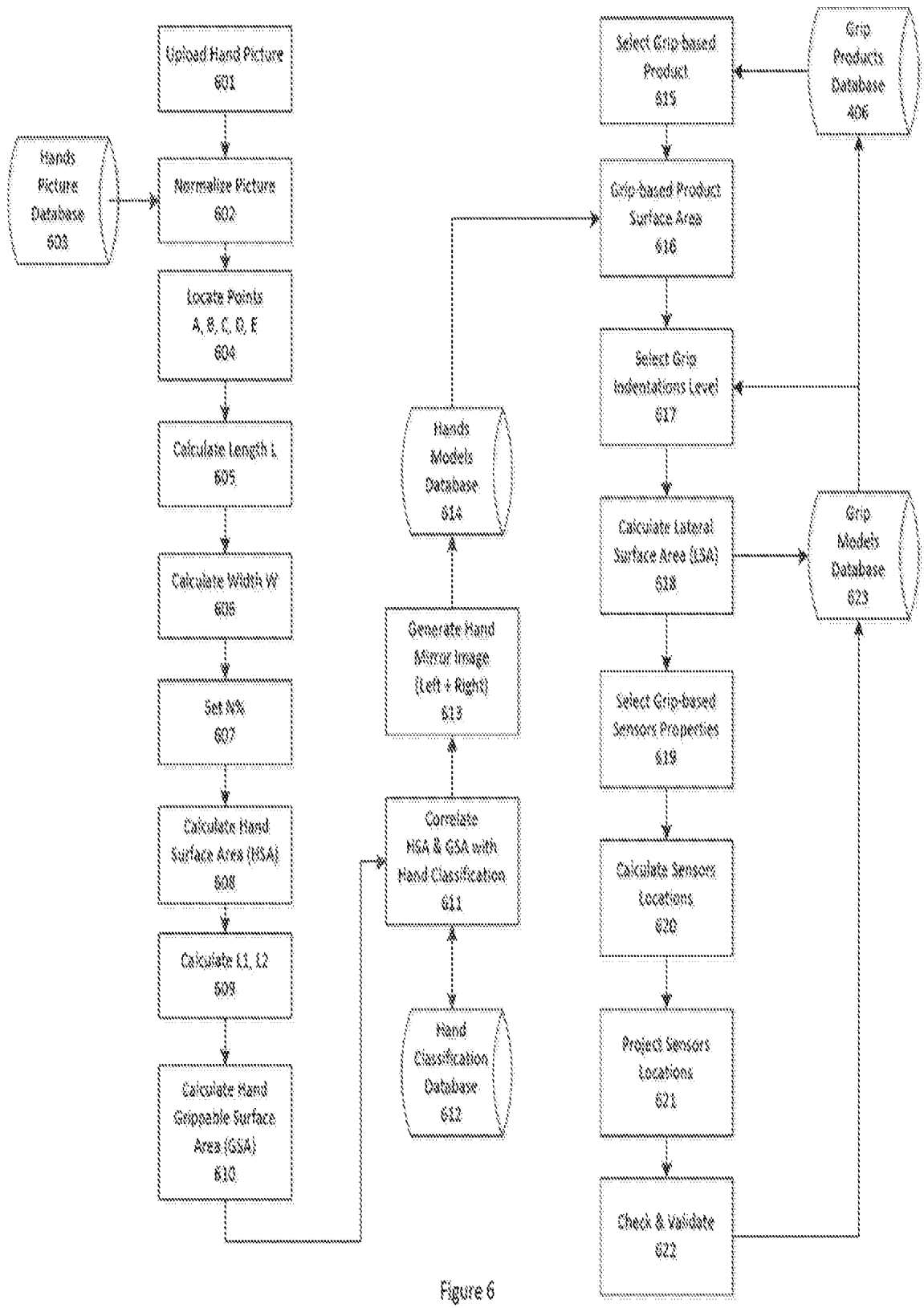
FIG. 6 describes the flowchart for modeling connected grips.

FIG. 6 describes the hand to grip modeling classification flowchart.

Hand Modeling Process

The hand modeling process is typically implemented through a series of steps as listed thereafter.

Step 1 601 comprises the upload of a picture, or scan, of someone's hand into the hands picture database 603.

In the case of a scan, the scan process is providing a standard reference in the form of the paper format selected for that scan, be it A4, Letterhead or others.

In the case of a picture, a standard reference point is included into the picture to facilitate the normalization process, be it a coin, a ruler or some other object with known dimensions.

Step 2 comprises a normalization process 602 which validates the uploaded scan or picture by running an image process that cleans up the picture by adjusting its brightness and/or contrast as needed, re-orienting the captured hand into a fixed frame of reference for later processing, and saving it with specific file naming convention for archive and storage.

Step 3 comprises analyzing 604 the frame of reference of the picture of the hand to determine its referenced points A, B, C, D and E.

Step 4 comprises determining 605 the length L of the hand, as measured by the distance between referenced points E and D.

Step 5 comprises determining 606 the width W of the hand, as measured by the distance between referenced points A and C.

Step 6 comprises determining 607 the adjustment percentage N, as a mechanism to support hand size adjustments based on statistical analysis of previously computed hands to grip modeling. The value N is typically selected between a range of 0 to 5%, depending on the calculated length and width ratio.

Step 7 comprises computing 608 the total "hand surface area" HSA, using previously described equation.

Step 8 comprises determining 609 the value of L2, as measured by the distance between referenced points A and B, as well as determining the value of L1 as measured by the distance between referenced points B and C.

Step 9 comprises computing 610 the total "grip surface area" GSA, based on previously described equation.

Step 10 comprises correlating 611 the values of HSA and GSA to the hand classification database 612 in order to provide reference points for classification, such as the predefined categories defined as extra-small, small, medium, large and extra-large for examples.

Step 11 comprises generating a mirror image 613 of the captured hand in order to provide the referenced data points for both left and right hands.

Step 12 comprises storing the referenced data points into the hand models database 614, to be used by the grip modeling process.

Grip Modeling Process

Step 1 comprises the selection of the grip-based product 615 to be modeled from the grip product database 406. Each grip-based product is defined by its own set of requirements, such as number and type of required external and internal sensors, overall mechanical dimensions and internal rod structural requirements for examples.

Step 2 comprises retrieving 616 the previously computed hand "grip surface area" from the hand models database 614.

Step 3 comprises selecting 617 the desired level of indentations to be applied to the computation of the grip "lateral surface area" from the available grip models database 623. As described previously, selecting high level of indentations result in a relatively larger size increase compared to a low-level of indentations. Levels of indentations are typically pre-computed for a particular selection of hands and based on the ergonomic design required for a particular grip-based product, as described in the Section "Method for manufacturing ergonomic connected grips".

Step 4 comprises computing 618 the grip "lateral surface area" corresponding to the middle section 402 of the connected grip 101, based on previously described equation.

Step 5 comprises loading 619 the individual spatial sensors requirements that are associated to the selected grip product requirements. As noted previously, each external surface sensor is defined by a set of properties, including its required surface area, both in terms of geometric shape and size.

Step 6 620 and Step 7 621 comprise computing each sensor's location based on their individual requirements and project them onto the 3 dimensional "grip surface area" based on their respecting reference points, as calculated from the hand modeling process.

Step 8 comprises validating 622 that each sensor spatial requirements have been correctly projected on the 3 dimensional space by checking for instance for possible overlap between sensors surface area and spatial variations from the hand modeling process.

Step 9 comprises 623 storing the results of the above steps in the grip models database 623, effectively making all data points available to the connected grip manufacturing process.

Connected Grip Products Database

The connected grip models database 623 is established from a catalog of commercially available grip-compatible products 406, defined as commercial products built with one, or more, integrated connected grips 101 which are designed based on the previously described modeling process.

For example, a bicycle is defined as a commercial product which is using 2 connected grips integrated with its handlebar. Standard road drop handlebars, including track, cyclocross and touring bars, typically use a 23.8 mm griplever diameter, which is matched only to road bike type shifters or brake levers. The other common lever-grip size is used for mountain and city handlebars, including flat bars, riser bars, some porters bars, and others. On these bars, the lever and grip areas have typically a 22.2 mm diameter.

As another example, a ski pole is made of several parts, including a connected grip which is attached to the upper part of the pole's shaft with a strap. The pole's material is typically made of aluminum, carbon, wood or mixture materials such as carbon-kevlar composites. The pole shafts are typically using the same diameter at the top and bottom, with a diameter ranging from 10 mm up to 18 mm diameter or larger, based on the manufacturer specifications.

As yet another example, replacement handle grips for all brands of fitness and gym exercise equipment are commercially available online and in various retail stores. The replacement grips physical dimensions are defined by the bar sizes, lengths and most importantly radius of the equipment that these grips have to integrate with. For instance, 14 inches long times 1.25 inch diameter high density rubber handle grip are typically used on exercise equipment handle bars to provide a non-slip surface with a soft touch. A grip this size can be found on stabilization bars on treadmills, elliptical trainers, and the like.

As yet another example, the manufacturer of a commercial product seeking to enhance such product with the addition of one or more customized connected grips, is uploading the original grip mechanical specifications for that product into the grip product database. Once uploaded, the grip modeling process calculates a set of connected grips that best fit for that particular product.

In above examples, the grip product database 406 leverages the known physical properties of existing grips and other grip-compatible commercial products to build a new set of connected grips replacements. By leveraging the known grip product specifications, such as its diameter and length for examples, the grip modeling process calculates the dimensions of the connected grips that best fit within the existing grip product database 406, and customize the connected grips 101 to integrate with the selected grip-based product, effectively retrofitting, or introducing, a whole range of commercial products with new connected applications and contextual analytic services.

As more connected grips 101 get modeled and integrated into the grip model database 623, the grip product database catalog 406 expends with support for more contextual B2B and B2C applications 105 and platform analytic services 106.

Mechanical Design

The connected grip mechanical enclosure integrates all the necessary parts and components that compose the connected grip devices.

Figure 7:
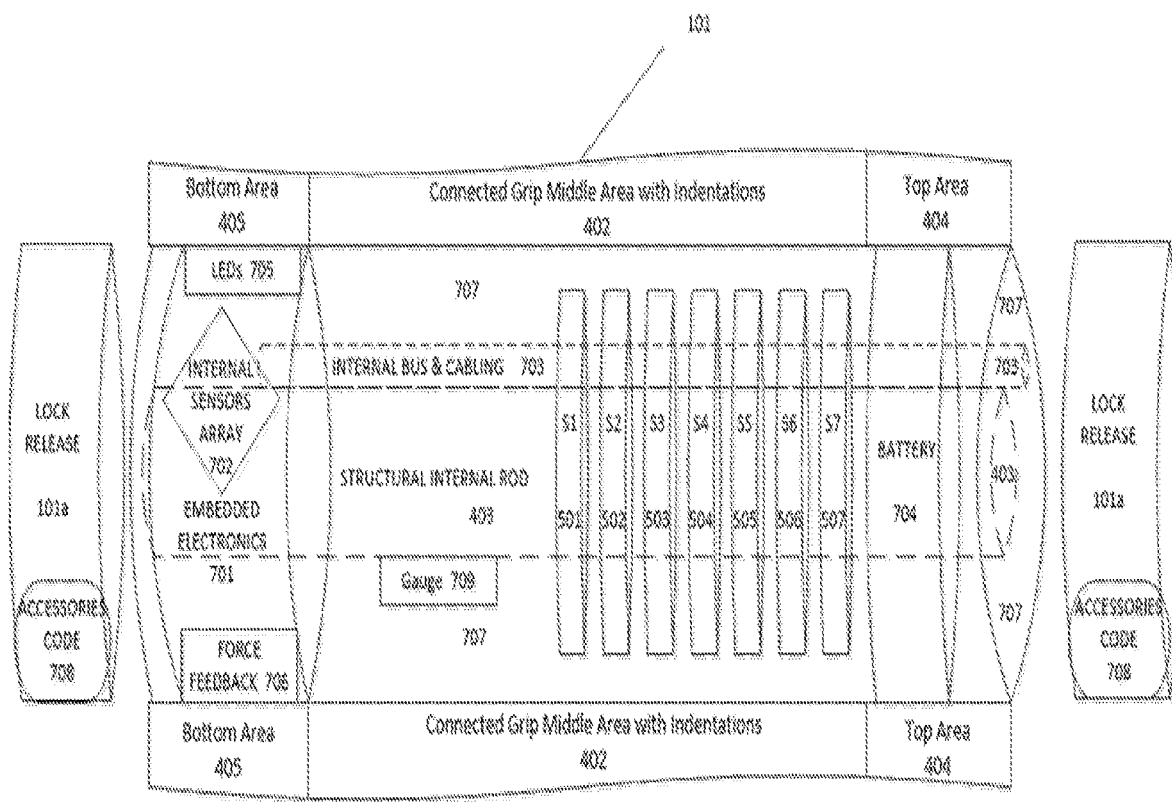
FIG. 7 illustrates a mechanical side view of a connected grip.

FIG. 7 illustrates a typical sideview of a connected grip.

As described in FIG. 7, the connected grip device 101 is architected from the following parts and components: Semi-customized ergonomic shell with programmable indentation levels 402; Programmable external surface sensors 501-507; Programmable internal sensors array 702; Rechargeable battery 704 for powering embedded electronics; Embedded electronics components and printed circuit board 701; Programmable LEDs 705, force feedback 706 and gauge sensors 709; Internal bus 703 to connect sensors and power to embedded electronics; Internal rod 403 to provide structural integrity to the connected grip; and Quick connect port 101a with code detection to support grip's accessories.

Method for Designing and Manufacturing Ergonomic Connected Grips

Step 1 comprises the capture of the desired level of indentations for a new connected grip 101. The process starts by selecting users whose hands size have already been processed and matched within the hand classification database 612. By having at least one user representative of each class, such as men, woman, child, small, medium and large for examples, this process insures that the ergonomic design of the new connected grip is going to match with the existing hand classification database 612.

Step 2 comprises asking selected users to tightly grip a soft material, such as clay for example, which is a physical representation of the grip-based product surface area dimensions 402, including its width W and radius R, without any indentations, and represented as a pure cylinder or other 3 dimensional objects. By tightly pressing the user's hand, palm and fingers into the provided clay module, the selected user is generating a set of imprints which are representative of the grip-based product to be made based on applicable hand classification and level of indentation.

Depending on the force exercised by a selected user when applying pressure to the clay module, the level of indentations becomes a variable that can be expressed as light, medium and high for examples, which is a reflection of the actual pressure applied by the individual fingers and palm of the hand of that selected user onto the clay module.

The result of Step 2 is the creation of a set of 3 dimensional grip molds, in clay or from other soft material, which are specific to a particular type of grip-based product, which are representative of the different physical hands that created them.

Step 3 comprises scanning each of the 3 dimensional grips molds using a 3D scanner, effectively generating a 3D digital representation of each mold. Computer aided design (CAD) software is then used to align and center the computed "grip surface area" dimensions with its desired computed surface sensor locations onto the 3 dimensional mockups. Finally, a rendering process is applied to smooth irregularities and other artifacts from the mold.

Step 4 comprises having a CAD software program splitting the 3 dimensional grip molds into 2 distinct parts along their central longitudinal axis. This process creates 2 distinct 3D printable files, one for each half section of a connected grip.

Step 5 comprises sending the 2 3D printable files to a 3D printer for actual printing. The result is creating 2 distinct mechanical grip sections that can be assembled together to form the new ergonomic connected grip.

Step 6 comprises adding the selected external surface sensors into their respective locations within the 2 half sections of the connected grip. Each external surface sensor is typically made of a container that is inserted and attached, typically using glue for example, into the already computed reserved space and location of the corresponding "lateral grip surface" area half section.

Each sensor surface container includes 2 or more wires, using a protocol such as I2C for example, that are used to receive commands and transport the sensor captured analog or digital data to the micro-controller in the embedded electronic system. The sensors cables run inside the internal bus and cabling rod 703, parallel to the internal rod 403.

Step 7 comprises having all the external surface sensors, such as S1 501, S2 502, S3 503, S4 504, S5 505, S6 506 and S7 507 for examples, as well as the selected internal sensors array 702, such as accelerometers 813, gyroscope 812, humidity level 811, ambient light 816, force feedback 706 and LEDs 705 for examples, successfully added and connected to the embedded system micro-controller 701.

Step 8 comprises having the remaining connected grip components, such as its wireless radio, such as cellular data or WiFi 805a, GPS 805b, Bluetooth 805c and battery 704 being added and connected to each other.

Step 9 comprises assembling back the 2 half grip sections, forming a single ergonomic connected grip device 101.

Step 10 comprises fully testing and validating the newly assembled connected grip ergonomic device 101.

Step 11 comprises finalizing all grip 3D and other mechanical files that for enabling volume manufacturing.

Hardware and Software Stack

The connected grip 101 is architected around an embedded electronic platform controlled by software kernel, drivers and local embedded applications.

Figure 8:
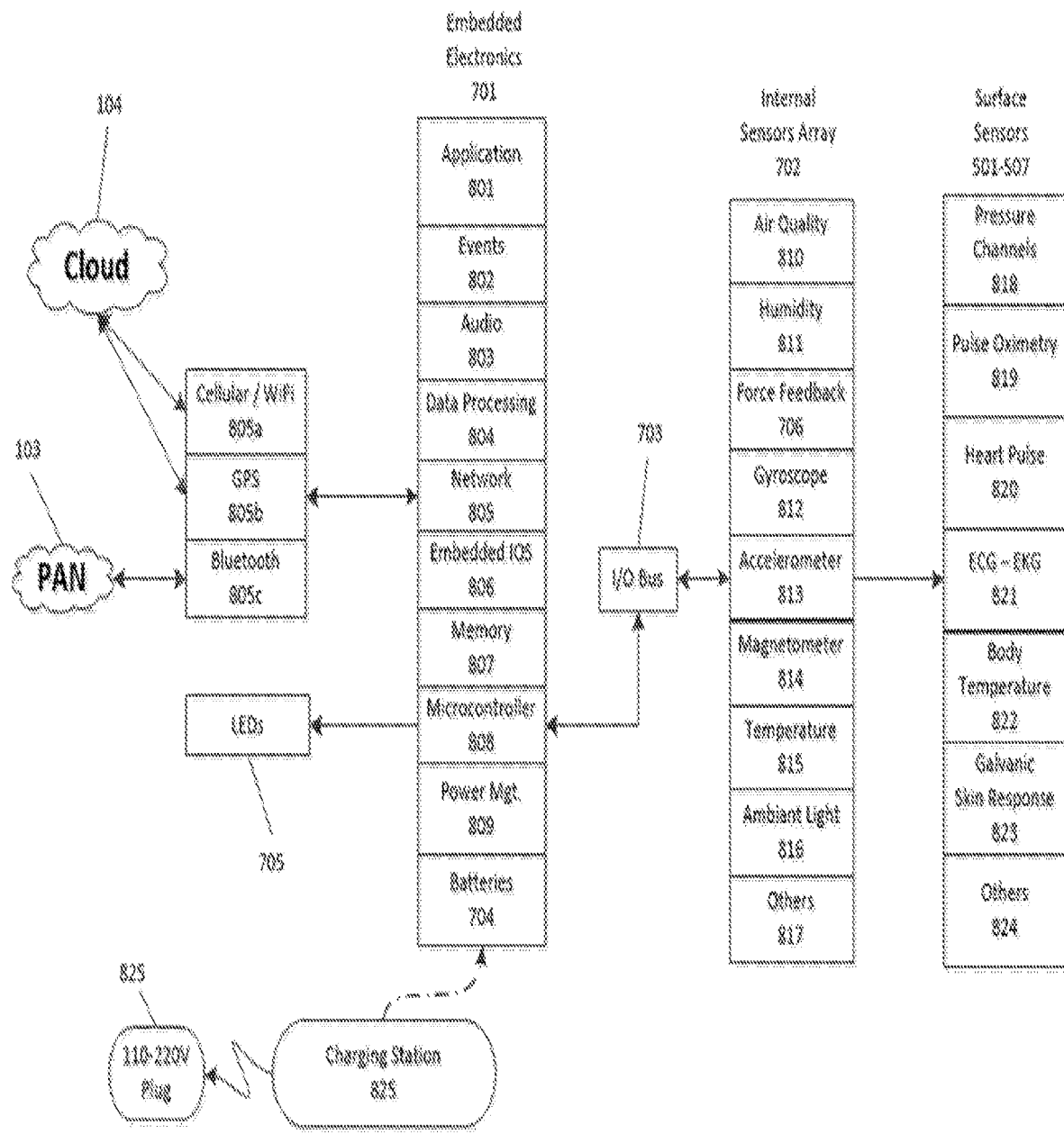
FIG. 8 describes the hardware and software stack of a connected grip.

FIG. 8 describes the hardware and software stack of a connected grip.

The embedded electronic 701 includes a micro-controller 808 with supporting circuitry, including memory 807, network 805, power management 809, micro-kernel operating system 806, data processing 804, audio feedback 805, events management 802, embedded applications 810, as well as all the physical internal and external sensors connected to it over the I/O Bus 703.

The internal sensors array 702 include sensors such as accelerometers 813, gyroscope 812, magnetometer 814, ambient temperature 815, force feedback 706, humidity level 811, air quality 810, ambient light 816 and gauge pressure 709 for examples. Additional sensors 817 can be added, or removed, using the internal I/O Bus 703.

The external surface sensors 501-507 include sensors that are in close proximity to, or touching, the skin of the user while engaging with a connected grip 101, including for instance force pressure channels 818, pulse oximetry 819, heart rate pulse 820, ECG-EKG 821, body temperature 822 and galvanic skin response 823, for examples. Additional external surface sensors 824 can be added, or removed, using the I/O bus 703.

There may be no external ports or cables in a connected grip in order to provide a completely waterproof and ruggedized device. As a result, connected grips may be recharged using a separate stand-alone magnetic inductance coil that plugs into a power plug. Typical examples of this technology may be found on devices such as high-end toothbrushes, smartphones and even kettles. Other recharging implementation maybe implemented by using a charging station 825 to directly power the connected grip 101 while connected to a wall outlet via a power plug 825.

The default network connection 805 is implemented via Bluetooth 805c with optional support for GPS 805b, WiFi and Cellular Data 805a as needed, based on type of activity, internet connection and overall connected grip-based product specification.

The built-in LEDs 705, audio 803 and force feedback 706 provide information and notifications back to the user when interacting with a connected grip. The events management 802 that triggers the LEDs, audio and/or force feedback are controlled by the embedded application 801 based on programmable threshold values computed by the paired mobile application 305 and platform analytic services 106. This implementation provides real-time and/or delayed feedback to the user based on current and past activities as captured from the connected grips.

Connected Grip Internal Sensors

The following is a non-exhaustive list of internal sensors which are embedded into the connected grips based on the desired product specifications.

The 3-axis accelerometer 813 is a sensor that measure acceleration in three separate axis, expressed at the rate of change of the velocity of an object. They measure in meters per second squared (m/s$^2$) or in G-forces (g). A single G-force on planet Earth is equivalent to 9.8 m/s$^2$ and vary slightly with elevation.

The 3-axis gyroscope sensor 812 allows the calculation of orientation and rotation, giving software developers measurement of 3-D motion with higher precision, accuracy and responsiveness.

The 3-axis magnetometer 814 sensor measures magnetic fields in three directions—or axes, labeled X, Y, and Z. In its most simple form, the sensor is used as a basic compass to find earth's magnetic north. Connected grips rely on this 9-axis combination to capture and model activities from users when interacting with connected grip-enabled products.

The ambient light sensor 816 typically captures the level of natural light. This particular type of sensor is also being used to measure the quality of someone's grip. For instance, when located within the grip surface area S6, this sensor is going to be covered by the palm of the user while interacting with the connected grip. As such, the measured level of ambient light is expected to be very low given that most light should be blocked by the palm of the user. The quality of the grip is then inferred by the level of measured light at all times during the interaction, providing actionable feedback to the virtual assistant and other application services.

The ambient temperature sensor 815 captures the temperature of the surrounding environment; technically, the temperature of the air surrounding a connected grip.

The gauge or pressure internal contact sensors 709 are typically ultra-compact absolute piezo resistive sensors that are located between the internal rod 403 and the mechanical enclosure 707 of the connected grip 101. They are effectively measuring pressure applied when the internal rod deforms slightly when an external force is applied to it by a user when interacting with weights, chest extender or elastic band activities, for examples.

The barometric pressure sensor 817 typically measures the pressure between a range of 600 to 1100 millibar. This range equates to from below sea level up to 12,000 feet above sea level.

The humidity sensor 811 typically detects relative humidity, measuring both air temperature and moisture. Relative humidity, expressed as a percent, is the ratio of actual moisture in the air to the highest amount of moisture air at that temperature can hold. The warmer the air is, the more moisture it can hold, so relative humidity changes with fluctuations in temperature.

The force feedback sensor 706 recreates the sense of touch by generating programmable vibrations within a connected grip. This mechanical stimulation is used to provide direct feedback to the user when interacting with a connected grip. The type of force feedback, such as starting time, duration and vibration strength for examples, is controlled by software running in the embedded electronics 701. This enables feedback to be provided dynamically to the user based on real-time sensors data analytic. Force feedback 706 is also used in combination with LEDs 705 and audio 803 sensors to synchronize and combine different types of feedback as needed.

The LEDs feedback sensors 705 provide visual feedback to the user before, during and after interacting with connected grips. LEDs are controlled dynamically by software running on the embedded system and used to provide a variety of information back to the user such as choice of color, blinking frequency or color rotation for example. For instance, LEDs are used to provide feedback when connecting a new accessory to a connected grip. By switching the LED color from red to blue, for example, the user is getting the confirmation that the new accessory is properly attached and recognized to the connected grip. As another example, a set of blinking red LEDs is used to indicate that the connected grip is not connected to either the personal area network or to the wireless networks. It is also expected that connected grips also provide visual feedback by lighting up from within their mechanical enclosure.

The specific combination of ambient light 816, ambient temperature 815, barometric pressure 817 and humidity sensors 811 provide valuable information on the environment of someone when interacting with connected grips. The captured data is particularly important as the level and quality of effort provided by a user when interacting with a connected grip cannot be accurately measured until correlated from the environmental data.

The above sensors are selected and integrated by default into the connected grips. Custom selection applied during the grip modeling process also offers the option to pick and choose each type of sensors to be integrated into a particular connected grip product based on the grip product specifications and requirements.

Connected Grip External Surface Sensors

The following is a non-exhaustive list of external surface sensors which are embedded into the connected grips based on the desired product specifications.

The external pressure surface sensor 818 is typically an ultra-compact absolute piezo resistive sensor. It includes a monolithic sensing element and an IC interface able to take the information from the sensing element and to provide a digital signal to the connected grip. The sensing element typically comprises a suspended membrane realized inside a single mono-silicon substrate capable of detecting pressure. The IC interface is manufactured using a standard CMOS process that allows a high level of integration to design a dedicated circuit which is trimmed to better match the sensing element characteristics.

The heart pulse rate 821 and pulse oximetry 819 sensors are designed to measure heart pulse rates and oxygen saturation level of the connected grip user's blood. The integrated optical sensor typically contains three green LEDs, one red LED, one infrared LED and one large-format photodiode, which is optically separated from the emitters by an opaque barrier. It works by shining light into the skin. Different amounts of light are absorbed by blood and the surrounding tissue. The light not absorbed is reflected to the detector. Absorption measurements with different wavelengths are used to determine the pulse rate and the saturation level of oxygen in the blood. Green light is best for measuring the pulse. Oxygen saturation in the blood is calculated from the different absorption rates of red (660 nm) and infrared (940 nm) light. The quality of the measurements depends to a large extent on the achievable signal-to-noise ratio and on the linearity of the photodetector. Tracking heart rate during a workout is a proven way to efficiently achieve goals.

The galvanic skin response (GSR) sensor 823 monitors the user's hand skin impedance and temperature under different situations. The skin conductivity changes with both changes in the underlying amount of perspiration released onto the skin from the sweat glands, and the number of active sweat glands.

The electrocardiogram (ECG) sensor 821 measures the electrical activity of the user's heart. Contrary to traditional ECG measurement systems that require the electrodes to be placed on each side of the heart for best possible measurement, an alternate implementation is used by combining the ECG sensors from a set of 2 connected grips, one from the left hand and the other from the right hand, providing data from both the left and right side of the body simultaneously and synchronously.

For less demanding ECG measurement, an alternate implementation can also be done using 2 fingers of the same hand, such as the index finger of the right hand touching the small finger of the same hand, with electrodes in between. Another alternate implementation is to locate the ECG-EKG sensors within the palm area S6 506.

The embedded electrocardiogram (ECG) sensors can also be used to recognize the unique cardiac rhythm of connected grip users. In doing so, the ECG sensors data are used to match the user's ECG against a stored profile database in order to authenticate the user's identity. The science is based on nearly a decade of R&D work at the University of Toronto, where researchers first began investigating an ECG biometric algorithm. In a connected grip, the authentication is done to match the recorded sensors data activities to the profile of a registered user.

The body temperature sensor 822 measures the temperature of the user's skin when holding a connected grip product.

Figure 9:
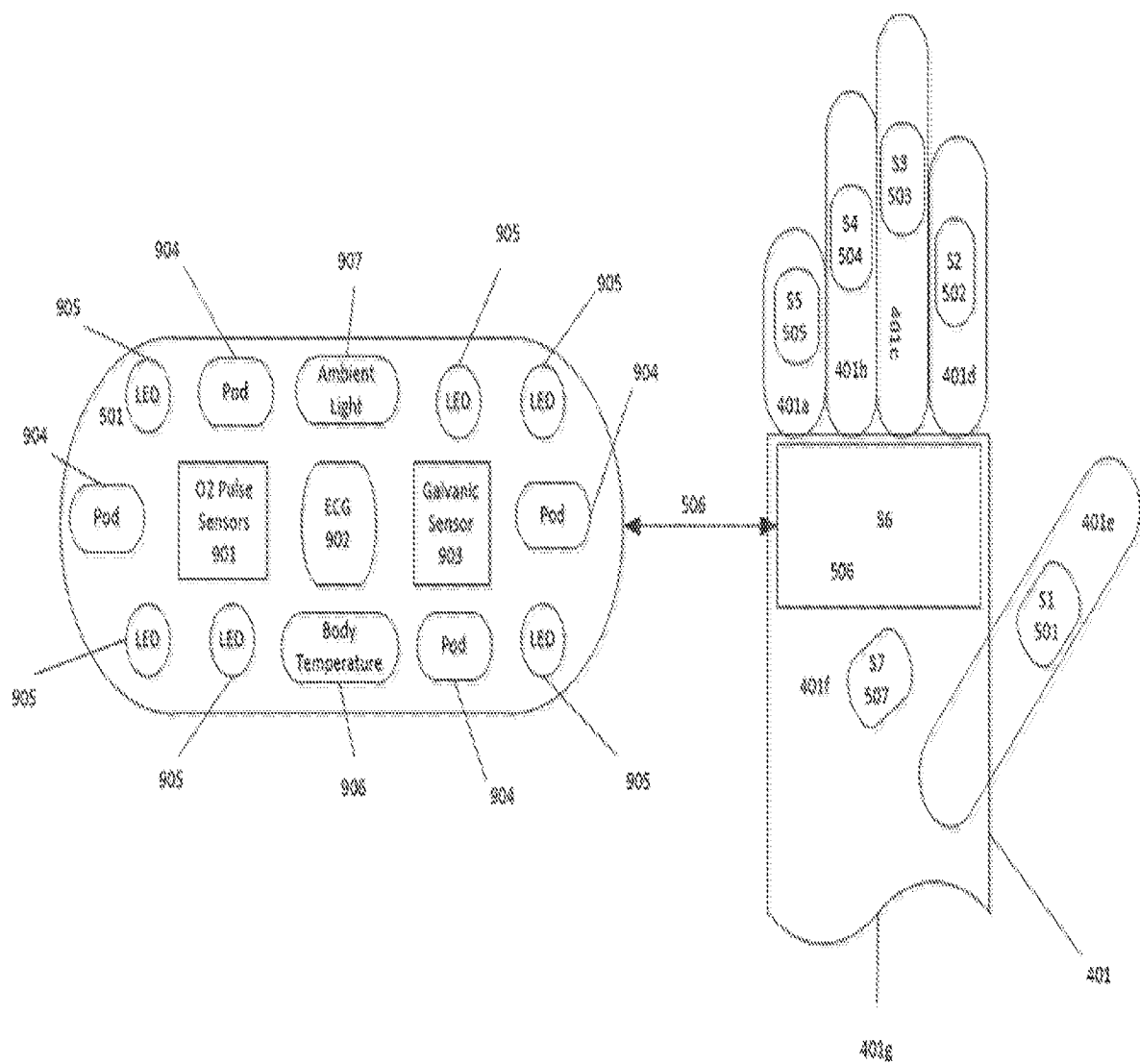
FIG. 9 illustrates the surface sensors of a connected grip.

The reference electrode pods 904, as listed in FIG. 9, provide references for the electrical measurements of pulse rate, oxygen level, galvanic skin response and ECG sensors. Their purpose is to maintain the correct DC bias potential between the human body and the connected grip embedded electronics.

Optional additional external surface sensors, such as touch fingerprint, can be combined with fingerprint recognition algorithm optimized for integration into consumer or professional connected grip-based products. Their small form factor, increased performance and flexibility are well suited for optional integration within connected grips based on grip product requirements.

As another example of additional external sensors, ultra-thin electronic skin sensors that stick to skin like a rub-on tattoo can send a mild electrical current over the skin to detect for example a user's blood sugar levels, without needles. This type of removable external sensor provides additional flexibility to the embedded connected grip sensors array by introducing a family of temporary disposable sensors that may be individually added and removed by the user or authorized care provider. This type of surface sensors is preferably located in one of the predefined connected grip external sensors areas or alternatively may also be attached directly to any skin surface area of the user's body. Depending on its specifications, it may not require any power or wired connection to the connected grip embedded system. Because of their built-in battery and wireless Bluetooth connectivity, this particular type of disposable skin surface sensor is discoverable by the paired registered user mobile application and as a result provides temporary additional specific sensor data to the connected grip overall data and contextual information systems.

The above external surface sensors are all selectable individually or as a group and can be integrated by default into the connected grip-based product. Custom selection applied during the grip modeling process also offers the options to pick and choose the particular type of external surface sensors to be integrated into a specific connected grip model, based on the overall grip product database specifications and requirements.

Location Example of External Surface Sensors

The location of the external surface sensors depend on the specific requirements for the connected grip-based product to be manufactured. For instance, it is possible to select a subset of the available external surface sensors based on the type of activities that need be supported for the particular grip product.

FIG. 9 illustrates possible locations for the external surface sensors.

As illustrated in FIG. 9, there are 6 external pressure sensors S1, S2, S3, S4, S5 and S7 located in their allocated computed surface areas 501, 502, 503, 504, 505 and 507, located respectively in the thumb 401*e*, index finger 401*d*, middle finger 401*c*, ring finger 401*b*, little finger 401*a* and palm area 401*f*.

The surface area S6, located in the palm area 506, is integrating because of its larger surface area the combined pulse oximetry 901, ECG 902, galvanic skin response 903, body temperature 906, ambient light 907 and related supporting components such as LEDs 905 and reference electrical pods 904.

In the above implementation, the external surface sensors are all integrated into a single connected grip-based product, leveraging all the available computed surface areas of that grip-based product.

Alternate implementation, such as a strength grip exerciser for example, may require only the various pressure sensors and not the other type of external surface sensors. By contrast, a health-based grip application may not require all of the pressure sensors but is likely to require all of the other external surface sensors.

Other possible implementations can also split the available external surface sensors between their left and right implementation when connected grips are used simultaneously. For example, the relatively large and more complex pulse oximetry O2 sensor 902 or galvanic skin response sensor 903 may be located either on the left or right connected grip but not necessarily on both.

Finally, the optional touch fingerprint sensor 824, or ECG-EKG sensors 902, can be used individually or jointly to authenticate users of connected grip-based products based on the B2B or B2C application requirements. When integrated, the touch fingerprint sensor is typically located as a replacement to one of the pressure sensors.

Connected Grip Hand Strength Exerciser

The grip strength is recognized as a good indicator of someone's health. When configured with external surface pressure sensors, a connected grip can be defined as a no-moving-parts hand strength exerciser. There is no spring or force an individual is battling against in order to squeeze and generate a force applied to a connected grip. This means that the connected-grip can be used for all levels of strength in one stand-alone packaged device and is therefore well suited to measure the strength from both the left and right hands of any users.

Benefits of Grip Strength Exerciser

Testing people's hand strength is a simple, low-cost way to screen them for the risk of heart attack or stroke as reported by several research studies that carried out large-scale studies into evidence that a firm hand grip is a rough yet reliable indicator of someone's good health.

One such study covered nearly 140,000 patients aged between 35 and 70 in 17 countries, whose health was monitored over four years. During checkups, the patients were asked to grasp a particular dynamometer, which measures muscle strength. Based on that study, every five-kilograms (11-pound) decline in grip strength was linked to a 16-percent increase in the risk of death from any cause over the study's four years. The decline was also associated with a seven-percent increased risk of a heart attack, and a nine-percent increased risk of a stroke.

Hand grip is a stronger forecaster of early death than systolic blood pressure, the study found. Grip strength reflects the sum of all of the healthy or unhealthy behaviors that users have engaged in throughout the course of their life even.

The use of a dynamometer for calibrating and use in a study like this, highlights the limitations and issues resulting in technology that is ancient and not easy to scale or transport. By contrast, connected grips are able to self-diagnose and calibrate without the need of engineers at remote locations. This allows for scaling and more easily obtainable reports to a wider audience.

Connected Grip as Grip Strength Exerciser

A connected grip is a no-moving-parts hand exerciser. Instead, the connected grip integrates multiple pressure sensors that are located on each fingers, thumb and palm area.

This unique combination of up to 7 distinct gauge pressure sensors enable a very specific and unique set of grip strength exercises that a user can perform at any point in time and under practically any conditions, be it walking, reading or watching TV. The operation of aggregating several sensor data-sets to form an overall strength of grip force is only achievable by either on-board or external processing analytics unit.

FIG. 10 shows the average grip strength table for both men and women.

As listed in FIG. 10, the hand grip strength of men and women is measured as a range of values expressed as pounds (lbs) or kilograms (kg) and rated based on excellent, very good, above average, average, below average, poor or very poor grip strength, for examples.

For example, men's grip strength measured at above 64 kg gets an excellent rating while grip strength of less than 40 kg gets a very poor rating.

As another example, women's grip strength measured at above 38 Kg gets an excellent rating while grip strength of less than 20 Kg gets a very poor rating.

The connected grip collects the pressure data as applied from each finger, or any combination of finger, over the time of a particular exercise session. The data is processed by an algorithm which filters and aggregates the data in order for the user to get a real-time visualization of strength activities.

In addition, the aggregated resulting data are compared against typical average grip strength for both men and women, as illustrated in FIG. 10. Based on user profile and historical data, a training program tailored to the recorded user's activities is generated by the platform analytic services to measure and provide support for continuing with regular grip strength activities.

This training program is provided by the virtual assistant, reminding and encouraging the user to reach its program goals while monitoring active sessions. The data recorded per session is also correlated against historical data to measure improvement over time and provide the user with comparison points over the course of days, weeks, months or years of grip strength activity.

Finally, access to micro-communities enables users to share data, program events and other information about their strength exercise as well as individual and collective activities.

Connected Grips Bundles and Product Offerings

Connected grips come in various types and shapes as indicated before based on the type of activities they are associated with. As such, connected grips can be marketed individually or in specific bundles that target particular set of activity.

Health Fitness Bundle

The Health fitness bundle comprises a "Gym-Trainer-in-a-Bag" that includes a pair of connected grips (left and right hands), set of color coded bands and accessories coupled with performance-enabling software applications to bring to market a highly innovative and effective method of working out to anyone looking to stay healthy and in shape from engaging in fun, relaxing and convenient activities done in the privacy of their homes while benefitting from recommendations of virtual assistants and communities of users.

The activities combined in the "Gym-Trainer-in-a-Bag" bundle comprise the following: Grip strength exerciser for left and right hands, Jump rope, Chest extender and expander, Weight trainer with individual arms or both grips locked, Arm(s) trainer, Leg(s) trainer, and Upper and lower body toning.

Health Fitness Bundles Catalog

The following is a non-exhaustive list of existing commercial and professional products which can either be retrofitted, or manufactured, with connected grips. The list includes the following: Golf clubs; Tennis rackets; Hockey sticks; Ski poles; Walking and hiking canes; Badminton rackets; Fishing rods; Swords; Bows; Canoe and kayak paddles; Fitness equipment (electrical machines, rowing systems, weight machines, etc.); Road bikes, bicycles, motor bikes; Guns; Knives; Vehicle steering wheels; Other physical sports requiring the user to grip on something; Virtual sport games (with the connected grip as a game controller); Virtual reality (with the connected grip as a Bluetooth remote controller); and other virtual applications.

While only selected embodiments have been chosen to illustrate the present invention, it will be apparent to those skilled in the art from the original disclosure that various changes and modifications can be made without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. A method, comprising:
   obtaining sensor data indicating grip strength for a user of a grip-strength exerciser comprising one or more grips, the sensor data comprising data from one or more sensors in the one or more grips as squeezed by the user's left hand and the user's right hand;
   analyzing the sensor data to identify a difference in the grip strength between the user's left hand and the user's right hand; and
   providing feedback to the user to compensate for the difference in the grip strength between the user's left hand and the user's right hand, comprising:
      generating a set of personalized activities for the user, the set of personalized activities being programmed to compensate for the difference in the grip strength between the user's left hand and the user's right hand; and
      delivering the set of personalized activities to the user, wherein the set of personalized activities comprises a physical activity to be performed by the user with the grip-strength exerciser.

2. The method of claim 1, wherein:
   the one or more grips comprise a first grip and a second grip;
   the user simultaneously squeezes the first grip in the user's left hand and the second grip in the user's right hand;
   the sensor data comprises first sensor data from one or more sensors in the first grip and second sensor data from one or more sensors in the second grip; and
   analyzing the sensor data comprises comparing the first sensor data with the second sensor data.

3. The method of claim 1, wherein the one or more grips consist of a single grip to be squeezed by the user's left hand and the user's right hand.

4. The method of claim 1, wherein:
   the one or more grips comprise a first grip;
   the first grip does not include any moving parts; and the one or more sensors comprise a plurality of pressure sensors in the first grip.

5. The method of claim 4, wherein the plurality of pressure sensors in the first grip comprises respective pressure sensors located in respective areas of the first grip corresponding to each finger of the user's left hand.

6. The method of claim 5, wherein:
the first grip is for the user's left hand;
the one or more grips further comprise a second grip for the user's right hand;
the one or more sensors further comprise a plurality of pressure sensors in the second grip; and
the plurality of pressure sensors in the second grip comprises respective pressure sensors located in respective areas of the second grip corresponding to each finger of the user's right hand.

7. The method of claim 4, wherein the plurality of pressure sensors in the first grip consists of up to seven pressure sensors.

8. The method of claim 4, wherein analyzing the sensor data comprises aggregating data from the plurality of pressure sensors to determine the grip strength for a respective hand of the user.

9. The method of claim 8, wherein analyzing the sensor data further comprises applying a rating to the grip strength for the respective hand of the user.

10. The method of claim 4, wherein the one or more sensors further comprise an accelerometer in the first grip.

* * * * *